United States Patent [19]

Ferruti et al.

[11] 4,067,876

[45] Jan. 10, 1978

[54] HIGH POLYMERS CONTAINING NICOTINIC ACID, PROCESS FOR THEIR PREPARATION AND THEIR USE

[76] Inventors: Paolo Ferruti, V.le Cassiodoro, 24; Rodolfo Paoletti, V.le Regina Margherita, 43, both of Milan, Italy

[21] Appl. No.: 622,442

[22] Filed: Oct. 14, 1975

[30] Foreign Application Priority Data

Oct. 15, 1974 Italy .................................. 28420/74

[51] Int. Cl.² ................................................. C08F 8/30
[52] U.S. Cl. .............................. 260/295.5 A; 526/50; 526/23; 536/1; 536/112
[58] Field of Search ................................... 526/50, 23; 260/295.5 A, 209 R, 209 D

[56] References Cited

U.S. PATENT DOCUMENTS 2,701,244   2/1955   Ham ........................................ 526/50

OTHER PUBLICATIONS

Chem. Abstracts, "Syntheses of Nicotinic Acid Derivative", Kataoka, 69294v; vol. 68, 1968.

*Primary Examiner*—William F. Hamrock
*Attorney, Agent, or Firm*—Stevens, Davis, Miller & Mosher

[57] ABSTRACT

Polymers having molecular weight between 1,000 and 1,500,000 characterized in that they contain radicals of nicotinic acid bound to the macromolecular structure by covalent bonds that are gradually hydrolyzed in biological environment by setting free nicotinic acid and non-toxic polymer residues.

9 Claims, No Drawings

HIGH POLYMERS CONTAINING NICOTINIC ACID, PROCESS FOR THEIR PREPARATION AND THEIR USE

The present invention is concerned with new polymers the characteristic of which is the presence of radicals of nicotinic acid bound with a polymeric matrix in such a way that they are hydrolyzed and they can form free nicotinic acid in biological environment.

More exactly, this invention refers to high polymers containing radicals of nicotinic acid bound with the macromolecular matrix through ester or amide bonds that are hydrolyzed gradually in biological environment.

It is known that the nicotinic acid has assumed great importance in human therapy in recent years as an agent capable of decreasing the cholesterol amount as well as the free fatty acids content in the blood plasma, and also as vasodilatator agent capable of efficiently curing also serious forms of arteriosclerosis.

However, it was found that the use of nicotinic acid causes serious troubles that are essentially due to the velocity at which this acid is metabolized which has led to the necessity that it be administered frequently up to a total daily dose of 3 to 6 grams. Usually this very high dose of nicotinic acid causes irritation to the gastric mucous membrane, or redness in general due to vasodilatation, or — as it happened in a significant number of patients — it provokes liver troubles in different degrees. Although these troubles disappear as soon as the treatment is interrupted, when they appear, it is recommended in general to stop the therapy.

We have now found that it is possible to prepare polymers containing certain percentages of radicals of nicotinic acid that are hydrolyzed only gradually in biological environment, thus permitting to maintain for long periods in the body pre-determined and constant quantities of nicotinic acid by only one administration. By so doing it is no longer necessary to frequently administer high doses of nicotinic acid of which only a very small portion is used in the body, whereas most of it is metabolized; consequently all collateral effects, that are undesired and connected with this kind of administration, are avoided.

Although in concept the solution to the problem as we found it seems plain in itself, it is instead in practice extremely difficult to find polymers: that have absolutely no toxicity; that are not metabolized, or that produce metabolites that in their turn are absolutely non toxic; that form, with the radicals of nicotinic acid bonds that in biological environment are only gradually hydrolyzed in the length of time desired.

Up to this moment we have found three classes of polymers that possess these characteristics; we also found that the only types of bonds between nicotinic acid and macromolecular structures capable of hydrolyzing in the way desired are the bonds of the ester or amide type.

These are the classes of polymers we have found:

A — Vinylic or vinylidenic polymers to which proper side chains are bound that contain free hydroxyl or amino groups capable of reacting with nicotinic acid.

Preferably the fundamental polymeric structure consists of polyacrylamide or polymethacrylamide, polyacrylic or polymethacrylic acid, whose nitrogen atom is mono-substituted with hydroxyalkylic chains, aminoalkylic chains or hydroxyaminoalkylic chains, The terminal hydroxy or amino groups of these chains have reacted with nicotinic acid that is thus bound to the macromolecular matrix through ester or amide bonds.

Characteristic polymers belonging to this class are shown below:

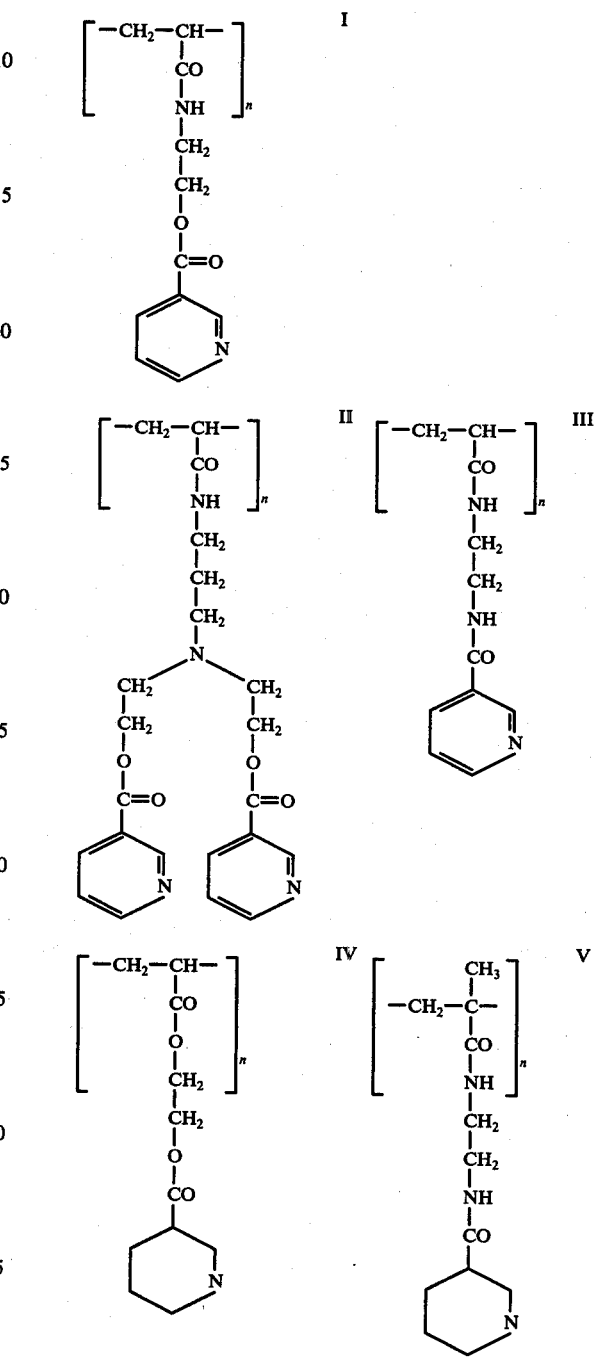

where $n$ is included between 10 and 5.000.

Homopolymers of types I, II, III, IV and V swell but are not water-soluble; therefore they are suitable only for certain kinds of administration.

In principle it is, however, always preferable to have water-soluble polymers.

To obtain polymers of the above kind that are water-soluble although they maintain all activity and toxicity characteristics unchanged, we have prepared copolymers containing, besides the units of polymers I, II, III, IV and V, also varying percentages of units that are markedly hydrophilic, such as for example those deriving from 1-acryloyl-4-methylpiperazine (VI), N-acryloyl morpholine (VII) and N-vinyl-pyrolidone (VIII):

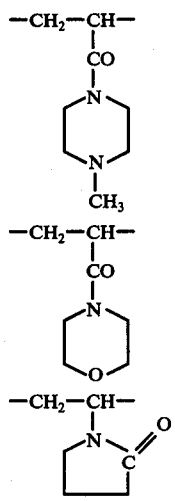

Homopolymers and co-polymers belonging to this class can be prepared by applying various methods which include:

a. preparation of the fundamental polyvinyl structure on which later the units are grafted that carry the amino and hydroxylic groups able to react with nicotinic acid and then reaction with nicotinic acid;

b. preparation of monomers consisting of the vinyl units and of the units carrying the amino and/or hydroxylic reactive groups; homo-polymerisation of these monomers or their co-polymerisation with the hydrosolubilizing units and finally reaction of the polymer obtained with nicotinic acid or one of its proper derivative, c. preparation of monomers consisting of the vinyl unit, of the unit carrying the amino and/or hydroxylic groups that are capable of reacting with nicotinic acid, and of the nicotinic acid itself, followed by homo-polymerisation of the monomers obtained or their co-polymerisation with the hydrosolubilizing units.

However, we have found that the method preferred when preparing the polymers of formulae I, II, III, IV and V under mild reaction conditions, and with nearly quantitative yield, consists of carrying out a radicalic polymerization of vinyl compounds containing activated amide or ester groups, in having the polymer so obtained react with a proper diamine, hydroxyalkyl-amine or alkylen-glycol and finally in having the free amino or hydroxyl present at the end of the side chains existing on the polymer react with a proper activated derivative of nicotinic acid.

The vinyl compounds most suitable for forming the macromolecular fundamental structure carrying the necessary activated groups are:

1-acryloyl benzotriazole; 1-acryloyl methoxybenzotriazole; 1-acryloyl methylbenzotriazole; 1-acryloyl imidazolide; N-acryloyl-succinimide; N-2,4,5-trichloro-phenil acrylamide.

Hydroxy and/or amino-compounds capable of reacting with the activated groups existing on the polyvinyl chain are preferably selected from the group comprising:

ethanolamine, N,N-bis (2-hydroxyethyl)-1,3-propandiamine, ethylenediamine, ethylene glycol.

The preferred reactive derivatives of nicotine acid, are: nicotinoyl chloride; nicotinoyl chloride hydrochloride; nicotinoyl imidazole; ethyl nicotinate.

Water-soluble co-polymers are prepared in quite a similar way as described for the homopolymers: in the first polymerization stage, instead of polymerizing only the activated derivatives of acrylamides, a mixture is polymerized containing the desired percentage of lyophilizing monomers preferably selected from the group consisting of 1-acryloyl-4-methylpiperazine, N-acryloyl morpholine, and N-vinylpyrolidone.

Polymerisation obviously is always of the radical type.

Polymers of type V, in which the fundamental structure is methacrylic, are instead preferably prepared by having alkylenediamine or hydroxyalkylenamine react with a proper derivative of nicotinic acid, preferably ethyl nicotinate; the N-nicotinoyl alkylenamine thus obtained is made to react with a reactive methacryloyl derivative, preferably with methacryloyl chloride.

In a particular case where use is made of ethylenediamine in the said way it is possible to obtain, for example, monomeric units having formula:

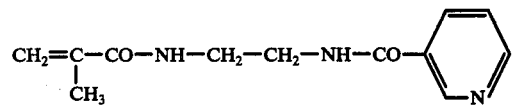

These monomeric units can be homopolymerized or co-polymerized with lyophilizing units of the type above mentioned in the presence of radical initiators.

B. Polyamide-amino structured polymers to which proper side chains are bound that carry hydroxylic groups esterified with nicotinic acid.

Polymers of this type are obtained by having bis-acrylamides which may be bis-acryloyl piperazine or bis-acrylamides having the formula:

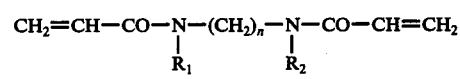

(where $n = 1-6$ and $R_1$ and $R_2$ being the same or different = hydrogen or alkyl radicals with 1-6 carbon atoms) reacted with hydroxyalkylmonoamines or hydroxyalkyldiamines having the formula:

(where $R_1$ and $R_2$ being the same or different are hydroxyalkyl groups and $n = 1-6$).

The reaction is carried out at temperatures in the range of 10° to 50° C and preferably in the presence of an inert solvent.

The polymers so obtained are made to react with nicotinoyl chloride, nicotinoyl chloride hydrochloride or with nicotinoylimidazole that esterify the free hydroxyls thus forming the polymers containing nicotinoyl radicals, according to the invention.

Characteristic polymers, according to this invention, are, for example:

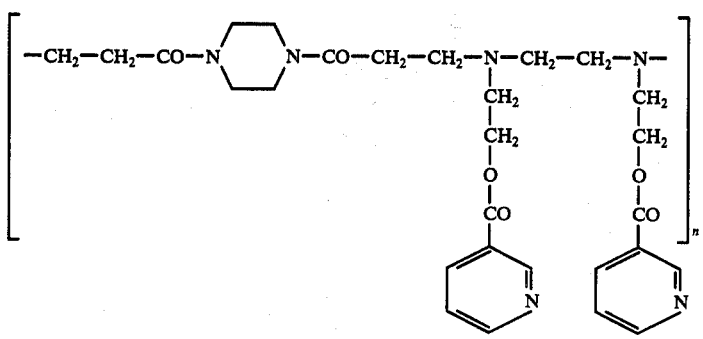

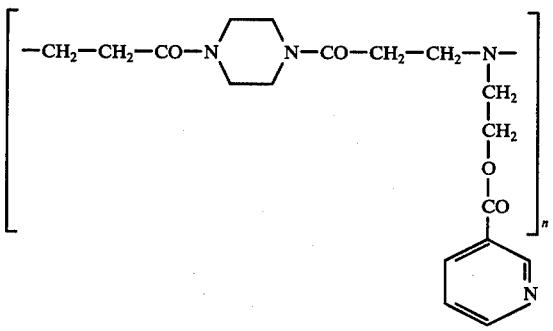

where n is included in the range from 5 to 1000 and which are obtained by reaction with nicotinoyl chloride hydrochloride or with nicotinoylimidazole of the products obtained from polyaddition of 1,4-bis-acryloylpiperazine and N,N'-bis (2-hydroxy ethyl)ethylendiamine or ethanolamine.

Polymers of this class can be water-soluble or water-insoluble. In the latter case it is always possible to make them water-soluble by co-polymerization with monomeric lyophilic units.

C—Polysaccharides obtained from dextrans of various origin and molecular weight, the free hydroxyls of which are esterified in whole or in part with nicotinic acid.

Polysaccharides to be used for preparing the polymers according to the invention can obviously be obtained by application of any known method. Their molecular weight is in the range of from 5,000 to 50,000. These polysaccharides can be esterified in whole or in part with reactive derivatives of nicotinic acid, such as nicotinoyl chloride, nicotinoyl chloride hydrochloride, nicotinoylimidazole.

Alternately, to obtain polysaccharides only partially nicotinized, polysaccharides that are totally nicotinized can be partially hydrolyzed. The polymers of classes A, B, C, according to this invention, have application in all the fields of human therapy where use is made of nicotinic acid, and the results that can be reached are therapeutically much more valuable without any undesired side-effect.

With the view to make the importance of the new invention more evident, we give below some significant pharmacological data.

The experiment whose results are reported was run on rats having average weight of 250 g; they were kept hungry for 48 hrs so as to artificially increase the free fatty acids rate in the blood. Rats were divided into three groups, one of which was the reference group, another was treated orally with 200 mg/kg of nicotinic acid (this is considered the maximum dose for nicotinic acid beyond which serious collateral effects occur); the other was orally treated with a quantity of polymer prepared according to Example 1, equivalent to 400 mg/kg of nicotinic acid.

|  | 1 h | 2 hrs | 6 hrs | 16 hrs | 24 hrs |
|---|---|---|---|---|---|
| Controls | 0.425 |  | 0.772 |  | 1.346 |
| Nicotinic acid | 0.303 | 0.375 | 0.720 | — | — |
| Polymer | 0.342 | 0.336 | 0.280 | 1.341 | 1.221 |

The quantity of free fatty acids in the blood plasma, expressed as $\mu Eq/ml$, was determined at the times indicated.

It is clear that while after 1 hour and after 2 hours the free nicotinic acid and the nicotinized polymer cause a drop almost equivalent in the free fatty acids level in the plasma (which means that during this time about 50% of the nicotinic acid, equal to 200 mg/kg, has been hydrolyzed from the polymer), after 6 hours the nicotinic acid is completely metabolised, thus it does not give any protection any more, whereas the polymer reaches the maximum of its efficiency; this is likely due to an additional gradual hydrolysis of the nicotinic acid bound to it. On an additional check run after 16 and 24 hours it was shown that at these limits of time all of the nicotinic acid bound to the polymer is already hydrolyzed and metabolized; it cannot, therefore, give any protection.

The animals treated with the nicotinized polymer do not show any sign of any undesired collateral effect.

In conclusion, it is clear from this experiment that with the new polymers it is possible to extend from 2 to at least 6 hours the protection furnished by the nicotinic acid by only one administration, without any undesirable collateral effect, because the so freed nicotinic acid evidently never exceeds the maximum dose tolerated by the body. Another experiment was run or rats weighing on an average 250 g each, but this time the free fatty acid increase in the blood was induced by administering nor-adrenaline (NA).

Rats were divided into four groups; one as reference group; another was treated with NA only; another group was treated with NA and after 30' with 800 mg/kg of free nicotinic acid; a group was treated with NA and after 30' with a quantity of the polymer of Example 1, equivalent to 800 mg/kg of nicotinic acid.

After 8 hours from NA administration, the animals were sacrificed and the free fatty acid rate in the blood determined.

By expressing such rate as $\mu$Eq/ml these values are found:

Controls — 0.370
NA — 0.768 ± 0.032
Nicotinic acid — 0.836
Polymer — 0.526 ± 0.030

From these data it is clear that even with extremely high doses of nicotinic acid it is impossible to maintain the fatty acid rate in blood plasma within the desired limits because, evidently, after a certain time it is anyhow metabolized. It is clear, instead that after 8 hours the nicotinized polymer acts still considerably by dropping very much the content of free fatty acids.

According to the invention, the new polymers can be administered orally as well as intravenously in any appropriate formulation. To make clearer the processes for preparing the polymers according to this invention, we give below some examples that have the purpose of merely illustrating this aspect of the invention:

EXAMPLE 1 a. A suspension formed of 18 g nicotinoyl chloride-hydrochloride finely dispersed in 350 ml of pure anhydrous chloroform is slowly added to a solution of 20 grams imadazole in 200 ml pure and anhydrous chloroform; temperature is maintained between −5 to 0° C by outer cooling.

Once the addition is finished the mixture is left to rest under agitation for 12 hours; then it is filtered and the solvent is made to evaporate under vacuum at 40° C. The residue is crystallized by cooling and crystallized again from anhydrous n-heptane. Yield 10 g (58%) of nicotinoyl imidazolide, m.p. 62° C.

b. To 17.3 g of poly-1-acryloylbenzotriazole (prepared for example according to P.Ferruti, A.Fere e G.Cottica, J.Polymer Sci., Pol.Chem.Ed. 12, 553 (1974)) dissolved into 150 ml of anhydrous N,N-dimethylformamide, 18.5 g of ethanolamine are added under stirring. Agitation is continued for 24 hours at room temperature. The reaction raw product is then poured into 500 ml ether; the precipitate is then dissolved in a little quantity of anhydrous methanol and then precipitated again with excess of ether.

This operation is repeated and the polymer thus obtained is dried until constant weight at ambient temperature and at 0.1 mmHg. Yield 11 g, (96%).

c. The previous polymer is dissolved in 100 ml N,N-dimethylformamide; to the mixture 18 g of nicotinic acid imidazolide are added. It is stirred until the solution is homogeneous and the reaction container is let to rest for 24 hours in a thermostatic bath at 65° C. After this time has elapsed, the reaction mixture is poured into ether, then the precipitate is dissolved in chloroform and it is reprecipitated with excess of ether thus obtaining 17 g (96%) of a polymer having the formula:

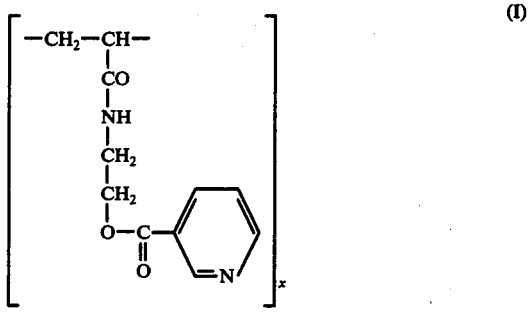

EXAMPLE 2

By operating as said in the first example, the treatment is made of 17.3 g poly-1-acryloylbenzotriazole dissolved in 150 ml of N,N-dimethylformamide with 48.6 g N,N-bis (2-hydroxyethyl)-1,3-propandiamine.

The product is isolated by pouring the reaction raw product into 1 liter of acetone and is purified as said before. Yield 20 g (92.5%).

Operating then as under Example 1, 20 g of polymer so obtained are treated with 34.6 g imidazolide of nicotinic acid, isolating therefore, as described under Example 1, 35.85 g of polymer having formula:

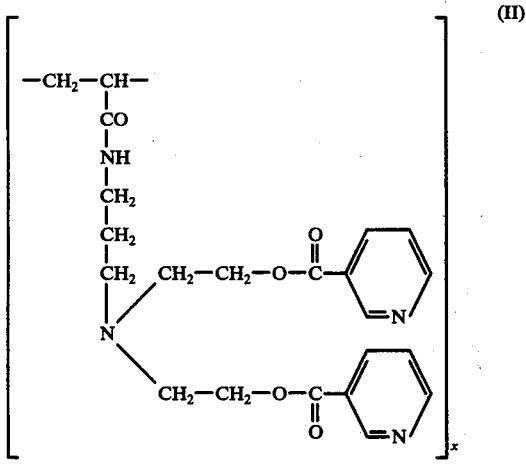

EXAMPLE 3

Operating exactly as described under Example 1 17.3 g. of poly-1-acryloylbenzotriazole and 25 g of ethylendiamine are reacted. The product is isolated as described under Example 1. Yield 10.5 g (92%). The polymer so obtained is treated under the same conditions of Example 1 with the same quantity of imidazolide of nicotinic acid and isolated in the same way. Yield 19 g (96%) of one polymer having the formula:

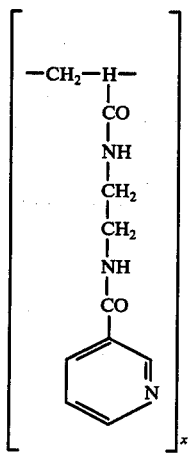

(III)

EXAMPLE 4

A mixture of 57 g ethyl nicotinate and 230 ml of ethylendiamine is made to reflux for 12 hours.

The excess of ethylendiamine and the ethyl alcohol thus formed are made to evaporate under vacuum; the residue is treated with anhydrous ether, thus obtaining 55.98 g (90%) of β-amino ethyl nicotinamide, melting point 54° C. 16.5 g of the previous prepared product are dissolved in 100 ml of anhydrous chloroform and 11.57 cc of triethylamine are added; the resulting mixture is added dropwise to a solution of 10.5 g of methacryloyl chloride in 50 cc of chloroform, maintaining the temperature between 0° and 5° C with outer cooling. Once the addition is finished it is left to rest under agitation for two hours at room temperature, then it is extracted three times in a separating funnel with portions each of 100 cc of a water solution of 20% NaCl; the chloroform phase is then separated; it is dried on $Na_2SO_4$, the solvent is made to evaporate and the residue is crystallized again from benzene, eliminating by warm filtration the traces of triethylamine hydrochloride that might still be present. Thus 11 g of (β-nicotinamidoethyl) methacrylamide, melting point 139° C, are obtained.

10 g of the previously prepared product are dissolved in 70 cc of pure methanol; 10 mg of azobisisobutyronitrile are added and after eliminating the air by repeated evacuations and inlets of argon, the mixture is maintained under argon atmosphere in a thermostatic bath at 60° C for 24 hours. Once this time has elapsed, the reaction mixture is poured into 500 ml of ether, thus obtaining 9.7 g (97%) of a polymer having the formula:

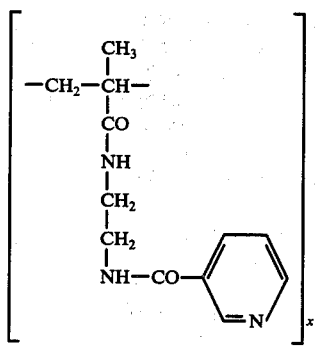

EXAMPLE 5 a. To a solution of 77 ml of acryloyl chloride in 350 ml of anhydrous toluene, 85.1 ml of N-methyl piperazine and 145 ml of triethylamine in 750 ml of anhydrous benzene are slowly added under agitation, while maintaining the temperature between −5° and 0° C by outer cooling.

This addition finished, 0.5 g of tert.-butyl catechol are added and the mixture is left under agitation at room temperature for one hour. The reaction mixture is then filtered; solvents are eliminated by evaporation at 40° C and 15 mm Hg and the residue is distilled; boiling point 100°–105°/0.4 mm Hg. Thus 57 g (50%) of 1-acryloyl 4-methyl piperazine are obtained.

b. Copolymers between acryloyl benzotriazole and 1-acryloyl-4-methyl piperazine have been prepared by dissolving the two monomers in the desired ratio into a proper solvent (for example dioxane), by adding a radical initiator (for example azobisisobutyronitrile) and by maintaining the mixture under inert atmosphere at 40°–80° C over 12–24 hours. Copolymers are then isolated by dissolving the reaction mixture with excess of n-heptane. then These copolymers have been then treated with ethanolamine and thereafter with imidazolide of nicotinic acid, in a way quite similar to that described under example 1, thus obtaining copolymers between I and 1-acryloyl-4-methyl piperazine.

In another case if we treat with N,N-bis(2-hydroxyethyl)1.3-propandiamine and then operate as specified under example 2 the corresponding copolymers between II and 1-acryloyl-4-methyl piperazine are obtained.

In a similar way, by treating with ethylendiamine and proceeding as indicated under example 3 copolymers of III are obtained.

By starting from copolymers between 1-acryloyl benzotriazole and N-acryloyl morpholine or N-vinyl-pyrolidone, that can be obtained in a way entirely similar to that mentioned above in the case of the 1-acryloyl-4-methyl piperazine, but replacing such monomers for the 1-acryloyl-4-methyl piperazine, and then operating as described in detail in the preceding paragraph, the copolymers between I, II or III and N-acryloyl morpholine or N-vinyl pyrolidone are obtained.

It is deemed superfluous to describe in particular the preparation of the above mentioned copolymers because the details given here and the description of examples nos. 1, 2 and 3 make it obvious for a man skilled in the art to prepare these products.

Copolymers between V and 1-acryloyl-4-methyl piperazine, N-acryloyl morpholine or N-vinylpyrolidone have been obtained directly from (β-nicotinamidoethyl) methacrylamide and those monomers, by radical copolymerisation in proper solvents such as methanol or dioxane, and isolating the products by precipitation with excess of ether.

EXAMPLE 6

To a solution of 17.3 g of poly-1acryloyl benzotriazole in 170 ml of pure and anhydrous chloroform, 22 g of mononicotinate of ethylene glycol and 15 g of triethylamine are added. The mixture is left to rest for 24 hours at 60° C in an inert gas atmosphere. After this time, the product is made to precipitate by dilution with excess of ether and then it is filtered and dried at room temperatures and 0.1 mm Hg.

Thus 22 g (99.5%) of poly (β-nicotinoyloxyethyl)acrylate are added, having the formula

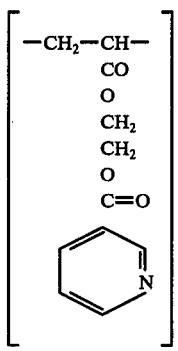 (IV)

Copolymers between β-nicotinoyloxyethyl acrylate and 1-acryl-4-methyl piperazine, N-acryloyl morpholine or N-vinylpyrolidone are obtained by following the same procedure but starting from corresponding copolymers of 1-acryloylbenzotriazole obtained as described under example 5.

EXAMPLE 7

A solution of 19.424 g of 1,4-bisacryloyl piperazine (prepared according to F.Danusso, P.Ferruti and G.Ferroni, Chimica e Industria 49, 271 (1967)) plus 14;821 g of N,N'-bis hydroxyethylethylendiamine in 250 ml of pure methanol is left to stay at room temperature for 72 hours.

After this time the reaction mixture is diluted with excess of ether, thus separating 34 g (99.3%) of polymers having this formula:

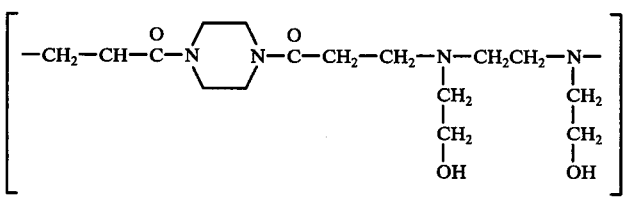

To a solution of 34 g of the polymer in 250 ml of pure and anhydrous chloroform, 50 ml of triethylamine are added and then slowly by little portions under agitation 45 g of finely powdered nicotinoyl chloride hydrochloride are also added. This addition finished, 40 ml of triethylamine are further added and left to stay while agitating for 8 hours.

The mixture is diluted with additional 200 ml of chloroform and the solution extracted four times with portions of 350 ml each of a water solution of 10% sodium chloride.

The chloroform phase is filtered and dried on anhydrous potassium carbonate; after separating the latter, the product is precipitated by dilution with large excess of ether.

The product is then dried at room temperature and 0.1 mm Hg. Thus 48.5 g (88%) of a polymer are obtained, having this formula:

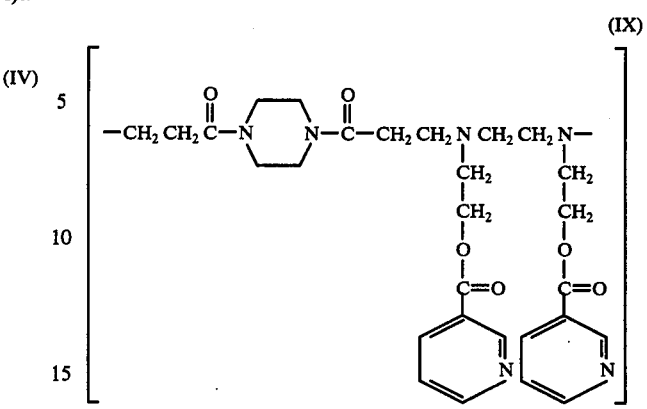 (IX)

EXAMPLE 8

A mixture consisting of 20 g of dextran (commercial product B.D.H. having average molecular weight in the range of 200.000 and 275.000), of 100 g nicotinoyl chloride hydrochloride and 500 ml pyridine is refluxed under stirring until a clear solution is obtained.

This solution is cooled, poured into excess of distilled water and the solid product precipitated is separated by filtration. This product is then purified by dissolution in chloroform and re-precipitated with excess of ether, thus obtaining 42 g (67.9%) of dextran where all of the free hydroxyls that were initially present have been esterified with nicotinic acid.

What we claim is:

1. Polymers having a molecular weight between 1,000 and 1,500,000 characterized in that they contain radicals of nicotinic acid bound to a polyvinylic macromolecular structure through hydroxyalkyl or aminoalkyl chains grafted thereon, with which it forms covalent bonds that are gradually hydrolized in biological environment by setting free nicotinic acid and non-toxic polymer residues, wherein the nicotinic acid radicals are bound to the chains grafted onto the macromolecular structure by means of amide or ester bonds, and wherein the polyvinylic macromolecular structure comprises polyacrylamide, poly-methacrylamide, polyacrylic acid or poly-methacrylic acid.

2. Polymers according to claim 1 characterized in that they are made water-soluble by means of copolymerisation with highly hydrophylic monomers.

3. Polymers according to claim 2, characterized in that the highly hydrophylic monomers are 1-acryloyl-4-methyl piperazine, N-acryloyl morpholine, or N-vinyl pyrolidone.

4. A process for preparing polymers as defined in claim 1 wherein the polyvinylic macromolecular structure is first prepared by polymerization under radical polymerization conditions of acrylamide, methacylamide, acrylic acid or methacrylic acid activated derivatives, and is thereafter reacted through hydroxyalkyl or aminoalkyl-chains previously grafted on it with nicotinic acid or a reactive derivative thereof.

5. A process according to claim 4 wherein polyvinylic macromolecular structure carrying activated groups is reacted with alkylene diamines alkylenehydroxyamine or alkyleneglycol and the free hydroxyl or amino groups of the new polymer are reacted with a compound selected from the group consisting of nicotinoyl chloride, nicotinoyl chloride hydrochloride, nicotinoyl imidazole, and ethyl nicotinate.

6. A process according to claim 5 wherein the polyvinylic macromolecular structure carrying activated groups is prepared by copolymerizing a monomer selected from the group consisting of 1-acryloyl benzotriazole, 1-acryloyl methoxybenzotriazole, 1-acryloyl methyl benzotriazole, 1-acryloyl imidazolide, N-acryloyl-succinimide, N-2,4,5-trichlorophenyl acrylamide with a lyophilic monomer selected from the group consisting of 1-acryloyl-4-methylpiperazine, N-acryloyl morpholine and N-vinyl-pyrolidone.

7. A process according to claim 5 wherein the polyvinylic macromolecular structure carrying activated groups is prepared by homopolymerizing a monomer selected from the group consisting of 1-acryloyl benzotriazole, 1-acryloyl methoxybenzotriazole, 1-acryloyl methyl benzotriazole, 1-acryloyl imidazolide, N-acryloyl-succinimide, N-2,4,5-trichlorophenyl acrylamide.

8. A polymer according to claim 1 of the formula

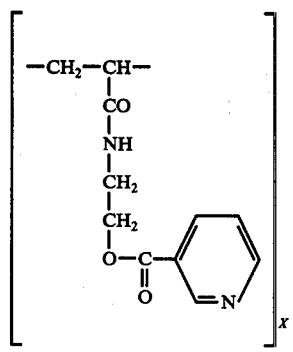

9. A therapeutic composition containing a therapeutically effective amount of a polymer as defined in claim 1.

* * * * *